United States Patent
Spijkerman et al.

(10) Patent No.: US 10,689,337 B2
(45) Date of Patent: Jun. 23, 2020

(54) FORMULATION OF DI(4-TERT-BUTYLCYCLOHEXYL) PEROXYDICARBONATE

(71) Applicant: NOURYON CHEMICALS INTERNATIONAL B.V., Arnhem (NL)

(72) Inventors: Geesje Klasina Spijkerman, Deventer (NL); Auke Gerardus Talma, Bathmen (NL); Markus Oliver Majoor, Amersfoort (NL); Antonie Den Braber, Arnhem (NL); Martin Hermanus Maria Jansen, Wijhe (NL)

(73) Assignee: NOURYON CHEMICALS INTERNATIONAL B.V. (NL)

( * ) Notice: Subject to any disclaimer, the term of this patent is extended or adjusted under 35 U.S.C. 154(b) by 0 days.

(21) Appl. No.: 16/220,106

(22) Filed: Dec. 14, 2018

(65) Prior Publication Data

US 2019/0185425 A1 Jun. 20, 2019

Related U.S. Application Data

(60) Provisional application No. 62/607,460, filed on Dec. 19, 2017.

(51) Int. Cl.
| | | |
|---|---|---|
| *C07C 407/00* | (2006.01) | |
| *C08K 5/14* | (2006.01) | |
| *C08K 5/12* | (2006.01) | |
| *C08K 3/36* | (2006.01) | |
| *C08L 31/02* | (2006.01) | |
| *C08L 67/00* | (2006.01) | |
| *C07C 409/34* | (2006.01) | |
| *C08L 33/08* | (2006.01) | |
| *C07C 69/78* | (2006.01) | |
| *C08L 67/06* | (2006.01) | |

(52) U.S. Cl.
CPC .......... *C07C 407/006* (2013.01); *C08K 3/36* (2013.01); *C08K 5/12* (2013.01); *C08K 5/14* (2013.01); *C08L 31/02* (2013.01); *C08L 67/00* (2013.01); *C07C 69/78* (2013.01); *C07C 409/34* (2013.01); *C08L 33/08* (2013.01); *C08L 67/06* (2013.01)

(58) Field of Classification Search
CPC ... C07C 69/78; C07C 407/006; C07C 409/34; C08K 3/36; C08K 5/12; C08K 5/14; C08L 31/02; C08L 33/08; C08L 67/00; C08L 67/06
See application file for complete search history.

(56) References Cited

U.S. PATENT DOCUMENTS

| | | | |
|---|---|---|---|
| 3,538,011 A | 11/1970 | van der Klaauw | |
| 2019/0248983 A1* | 8/2019 | Nagl | .................. C07C 407/006 |

FOREIGN PATENT DOCUMENTS

| | | |
|---|---|---|
| DE | 1 618 726 A1 | 4/1972 |
| DE | 10 2011 102 682 A1 | 11/2012 |
| WO | 2012/159726 A1 | 11/2012 |
| WO | 2017/089375 A1 | 6/2017 |

* cited by examiner

*Primary Examiner* — Christopher M Rodd
(74) *Attorney, Agent, or Firm* — Lorenz & Kopf, LLP

(57) ABSTRACT

Powder formulation comprising 20-75 wt % of di(4-tert-butylcyclohexyl) peroxydicarbonate and 25-80 wt % of ethylene glycol dibenzoate.

7 Claims, No Drawings

FORMULATION OF DI(4-TERT-BUTYLCYCLOHEXYL) PEROXYDICARBONATE

The present invention relates to a formulation of di(4-tert-butylcyclohexyl) peroxydicarbonate.

Di(4-tert-butylcyclohexyl) peroxydicarbonate is an organic peroxide that is used as initiator in various reactions, including the curing of thermoset resins—e.g. unsaturated polyester resins, vinyl ester resins, and methacrylic resins—and the polymerization of various monomers.

Thermoset resins, in particular unsaturated polyester and vinyl ester resins, are cured by reacting them with ethylenically unsaturated monomer, which reaction is initiated by an organic peroxide. The conventional ethylenically unsaturated monomer is styrene.

Di(4-tert-butylcyclohexyl) peroxydicarbonate is presently available as a powder in neat, undiluted form, and as pastes. The pastes generally contain about 40 wt % di(4-tert-butylcyclohexyl) peroxydicarbonate and further about 60 wt % of solvents (e.g. glycols) and dispersants and/or fillers.

Solutions of di(4-tert-butylcyclohexyl) peroxydicarbonate in an inert, phlegmatizing solvent have turned out to be unstable.

Neat di(4-tert-butylcyclohexyl) peroxydicarbonate is subject to re-classification in terms of fire class rating: from Class II to Class I (US storage classification NFPA 400). The lower the class, the higher the risks and the lower the amount of peroxide that is allowed to be stored on site.

Di(4-tert-butylcyclohexyl) peroxydicarbonate pastes have a Class III rating. However, pastes have the disadvantage of being difficult to pump into the resin composition. Pastes require specific, expensive pumps and emptying drums containing the pastes is rather problematic.

A solution to that problem would be dissolution of the paste in the ethylenically unsaturated monomer, prior to pumping it to the reaction mixture. Unfortunately, however, the presently used solvents in such pastes (glycols) are not compatible with styrene.

Hence, there is a desire to provide a di(4-tert-butylcyclohexyl) peroxydicarbonate formulation that dissolves in styrene and is rated Class II (US storage classification NFPA 400), which means that its burning rate is between 60 and 300 kg/min.

At the same time, the formulation should not segregate during storage.

WO 2017/089375 discloses di(4-tert-butylcyclohexyl) peroxydicarbonate formulations with reduced burning rate. As phlegmatizers, this document discloses, amongst others, glycerol tribenzoate and dilauroyl peroxide.

Dilauroyl peroxide, however, is hard to dissolve in a curable resin. Dissolution requires either the use of a co-solvent or heating. The latter has a safety risk. Furthermore, as shown in the experimental section below, the effect of glycerol tribenzoate on the burning rate is limited and can be further improved.

It has now been found that stable formulations with further reduced burning rate can be obtained by blending neat di(4-tert-butylcyclohexyl) peroxydicarbonate powder with ethylene glycol dibenzoate (EGDB).

The present invention therefore relates to a powder formulation comprising:
20-75 wt % of di(4-tert-butylcyclohexyl) peroxydicarbonate and
25-80 wt % ethylene glycol dibenzoate.

It is noted that U.S. Pat. No. 3,538,011 and WO 2012/159726 disclose the phlegmatization of dibenzoylperoxide, bis(2,4-dichlorobenzoyl)peroxide and cyclohexanon peroxide with some of these phlegmatizers. However, their effect on the burning rate of peroxides, let alone di(4-tert-butylcyclohexyl) peroxydicarbonate, is neither disclosed nor suggested.

The formulation according to the present invention is preferably prepared by blending neat di(4-tert-butylcyclohexyl) peroxydicarbonate powder with EGDB. In a preferred embodiment, part of the EGDB is added to a mixing device, after which the peroxide is added to the mixing device. The remaining part of EGDB is added to the mixing device after the peroxide has been added.

Before blending, EGDB can be milled, preferably such that 90 vol % of the particles has a size (d90) less than 500 microns, more preferably less than 400 microns, more preferably less than 300 microns, and most preferably between 150-250 microns. Smaller particles entail health and explosion risks due to dust formation. Larger particles are difficult to dissolve in a resin.

The neat di(4-tert-butylcyclohexyl) peroxydicarbonate powder preferably contains particles with a size (d90) less than 100 microns, and most preferably 10-40 microns.

Despite the significant difference in particle size between the peroxide and EGDB, it is—surprisingly—possible to obtain stable, non-segregating formulations of these two components.

In contrast to conventional techniques for making peroxide formulations (such as in-situ preparation of the peroxide in a phlegmatizer or mixing of a phlegmatizer with an aqueous suspension of the peroxide), the above method allows for higher peroxide concentrations in the formulation. Furthermore, no drying steps are required since water is absent.

The formulation according to the present invention comprises 20-75 wt %, preferably 50-75 wt %, and most preferably 60-70 wt % di(4-tert-butylcyclohexyl) peroxydicarbonate; calculated as neat peroxide.

The formulation according to the present invention comprises 25-80 wt % preferably 25-50 wt %, and most preferably 30-40 wt % of EGDB.

EGDB is solid at room temperature (20° C.), has a melting point above 50° C., and is soluble in unsaturated polyester resins.

The formulation according to the present invention preferably also comprises one or more anti-caking agents, in a preferred amount of 0.1-5 wt %, preferably 0.5-2 wt %, most preferably 0.8-1.2 wt %, based on EGDB. Conventional anti-caking agents can be used. A preferred anti-caking is silica.

The powder formulation according to the present invention is preferably free of substantial amounts of other components.

The formulation of the present invention can be used in polymer modification processes, cross-linking reactions, (mass) polymerization processes, and curing processes of, for example, unsaturated polyester resins, vinyl ester resins, and acrylate resins, including ortho-resins, iso-resins, iso-npg resins, and dicyclopentadiene (DCPD) resins. Examples of such resins are maleic, fumaric, allylic, vinylic, and epoxy-type materials.

Curing processes using the formulation according to present invention are preferably performed at temperatures in the range 60-140° C. Examples of suitable curing techniques are SMC, BMC, pultrusion, filament winding, cured-in-place pipe (CIPP), and the manufacturing artificial stone.

EXAMPLES

Reference Example 1

Ethyleneglycol dibenzoate (EGDB) flakes were milled to a d90 particle size of about 225 microns.

Different amounts of silica (MFIL-P(S), ex-Madhu Silica) were added after said milling.

The influence of silica on caking of EGDB was studied with caking tests, which were performed as follows.

Cylinders with a diameter of 40 mm diameter were filled with 30 gram EGDB. On top of the material, a weight was placed of either 240, 300, or 500 grams. The cylinders were stored in an oven for 48 hours, at either 30° C. or 40° C.

After cooling down, EGDB was removed from the cylinders and caking was judged visually. The results are displayed in Table 1, in which:
"severe caking" means: the cake remained a cake after removal of the cylinder and was hard to break up;
"caking" means: the cake remained a cake after removal of the cylinder but was easy to break up;
"slight caking" means: the cake broke during removal of the cylinder, but small, easy to break up lumps remained;
"no caking" means: the cake broke during removal of the cylinder and no lumps remained.

TABLE 1

| T (° C.) | Weight (g) | Silica (wt %) | | | | |
|---|---|---|---|---|---|---|
| | | 0 | 0.25 | 0.5% | 0.75 | 1 |
| 30° C. | 240 | ND[1] | ND | ND | No caking | No caking |
| 30° C. | 300 | | | | No caking | No caking |
| 30° C. | 500 | | | | Slight caking | No caking |
| 40° C. | 240 | Severe caking | Caking | Caking | No caking | No caking |
| 40° C. | 300 | Severe caking | Caking | Caking | No caking | No caking |
| 40° C. | 500 | Severe caking | Caking | Caking | Slight caking | No caking |

[1]ND = not determined

Example 2

Five formulations were prepared, each comprising di(4-tert-butylcyclohexyl) peroxydicarbonate and either (i) EGDB or (ii) EGDB containing 1 wt % silica as prepared in Example 1:

Formulation A comprising 60 wt % di(4-tert-butylcyclohexyl) peroxydicarbonate in EGDB.
Formulation B1 comprising 70 wt % di(4-tert-butylcyclohexyl) peroxydicarbonate in EGDB.
Formulation B2 comprising 70 wt % di(4-tert-butylcyclohexyl) peroxydicarbonate in EGDB comprising 1 wt % silica as prepared in Example 1.
Formulation C1 comprising 80 wt % di(4-tert-butylcyclohexyl) peroxydicarbonate in EGDB.
Formulation C2 comprising 80 wt % di(4-tert-butylcyclohexyl) peroxydicarbonate in EGDB comprising 1 wt % silica as prepared in Example 1.
Formulation D comprising 70 wt % di(4-tert-butylcyclohexyl) peroxydicarbonate in glycerol tribenzoate.

These formulations where prepared by first de-agglomerating EGDB and GTB flakes in a Retsch hammer mill (type SK-1, rotational speed: 2800 rpm, Sieve: 1.5 mm), followed by mixing di(4-tert-butylcyclohexyl) peroxydicarbonate (Perkadox® 16, ex-AkzoNobel) with the de-agglomerated powder in a Kitchenaid Heavy Duty mixer, type K5SS, for 5 minutes.

Formulations B1 and B2 were subjected to a segregation test.

A sample was charged into a 15° tilted cylinder (stainless steel, 50 cm length, 10 cm diameter) and slowly rotated (7-8 rpm) around it's longitudinal axis. After 20 minutes, rotation was stopped and samples were taken from the upper, middle and lower part of the cylinder.

The peroxide content of all samples was determined by iodometric titration, by dissolving the sample in THF, adding KI, and titrating with sodium thiosulphate. The results (see Table 2) show that the samples differed in less than 5%, meaning that the tendency for segregation is negligible.

TABLE 2

| | Formulation B1 | Formulation B2 |
|---|---|---|
| Overall formulation | 69.8 | 70.2 |
| Upper layer | 69.6 | 70.0 |
| Middle layer | ND | 70.1 |
| Lower layer | 70.7 | 69.5 |

[1]ND = not determined

Example 3

In order to study the solubility of the formulations in different resins and in styrene, 0.5 grams of the formulations were added to a 100 ml beaker containing 50 gram resin or styrene and stirred with an overhead pitched blade stirrer (40 mm) at 4 rpm. Dissolution speed was judged visually. The results are compared with that of neat di(4-tert-butylcyclohexyl) peroxydicarbonate.

The following resins were used:
Palatal® P4 (a styrene-containing unsaturated polyester resin ex-DSM)
Duracon® 205 (an acrylate resin ex-Polyplastics)

Table 3 shows that the formulations all dissolve as quickly as or even quicker than neat di(4-tert-butylcyclohexyl) peroxydicarbonate.

TABLE 3

| | Dissolution speed in: | | |
|---|---|---|---|
| | Palatal ® P4 | Duracon ® | styrene |
| neat | 10.5 min | 3.5 min | <10 sec |
| Formulation C1 | 10.5 min | | |
| Formulation B1 | 8.0 min | 3.0 min | |
| Formulation A | 6.0 min | | <10 sec |

Example 4

Neat di(4-tert-butylcyclohexyl) peroxydicarbonate and formulations A, B1, C1, and D were subjected to burning tests. In these tests, 20×2 cm strips of the formulations were made on a flat stainless steel plate.

The strips were ignited by a yellow gas flame. The time required to burn the entire 20 cm strip was measured and listed in Table 4.

TABLE 4

| formulation | Time (sec) |
|---|---|
| A | 55 |
| B1 | 18 |
| C1 | 11 |
| D | 6 |
| neat | 5 |

Example 5

Formulations B2 and C2 were subjected to external fire tests by the German Bundesanstalt für Materialforschung und-prüfung (BAM) in order to determine the burning rate and the corresponding storage.

Of each formulation, 17 packages (4G cardboard boxes with an inner plastic bag) were provided, each package containing 11.34 kg formulation.

One package was placed on one wooden pallet and surrounded with wood wool. The wooden pallet and the wood wool were ignited using a mixture of liquid fuels and an igniter. The irradiance was measured using infrared sensors arranged in pairs. The irradiance is a measure for the burning time, which can be used to calculate the burning rate.

The same experiment was repeated with six packages on one pallet and with ten packages on one pallet.

The burning rate of formulation B2 was 237 kg/min, which means that it is classified as US (NFPA 400) Class II (burning rate between 60 and 300 kg/min).

The burning rate of formulation C2 was 1018 kg/min, which means that it is classified as US (NFPA 400) Class I (burning rate between above 300 kg/min).

Example 6

To 100 g unsaturated polyesters resin (Palatal® P4), 100 g of quartz filler (Quarz Mehl M6) was added. After stirring, a peroxide (formulation) was added in an amount corresponding to 0.5 g neat peroxide.

The resulting mixture was poured into a test tube containing a thermocouple.

The test tube was heated in a water bath of 82° C. The temperature of the mixture was recorded in time.

The Geltime (GT) is the time required for the mixture temperature to increase from 63.3° C. to 85.6° C.

The time to peak (TTP) is the time required to reach the maximum temperature.

The peak exotherm (PE) is the maximum temperature reached.

The minimum cure time (MCT) is the time lapsed starting from 63.3° C. until the maximum temperature.

TABLE 5

| | | | | | | | |
|---|---|---|---|---|---|---|---|
| Palatal P4 (g) | 100 | 100 | 100 | 100 | 100 | 100 | 100 |
| Quarz (g) | 100 | 100 | 100 | | | | |
| Perkadox ® 16 (g) | 0.500 | | | 0.500 | | | |
| Formulation A (g) | | 0.794 | | | 0.794 | | |
| Formulation B1 (g) | | | 0.681 | | | 0.681 | |
| Formulation B2 (g) | | | | | | | 0.681 |
| GT (min) | 2.0 | 2.1 | 2.1 | 2.2 | 1.9 | 1.9 | 2.0 |
| MCT (min) | 3.7 | 4.0 | 3.9 | 4.4 | 4.1 | 4.2 | 4.1 |
| TTP (min) | 5.6 | 6.2 | 6.2 | 8.2 | 7.6 | 7.7 | 8.2 |
| PE (° C.) | 117.6 | 115.9 | 120.3 | 165.4 | 161.3 | 159.2 | 163.2 |

These results show that EGDB does not negatively influence the cure of polyester resins.

Example 7

Example 6 was repeated except that the temperature of the water bath was 70° C.

The results are displayed in Table 6, and again show that EGDB does not negatively influence the cure of polyester resin.

TABLE 6

| | | | | |
|---|---|---|---|---|
| Palatal P4 (g) | 100 | 100 | 100 | 100 |
| Quarz (g) | | | | |
| Perkadox ® 16 (g) | 0.500 | | | |
| Formulation A (g) | | 0.794 | | |
| Formulation B1 (g) | | | 0.681 | |
| Formulation B2 (g) | | | | 0.681 |
| GT (min) | 5.5 | 4.7 | 5.3 | 5.7 |
| MCT (min) | 8.8 | 8.0 | 8.4 | 8.8 |
| TTP (min) | 13.3 | 11.5 | 12.2 | 13.2 |
| PE (° C.) | 147.5 | 144.8 | 146.5 | 146.7 |

The invention claimed is:

1. Powder formulation comprising:
   20-75 wt % of di(4-tert-butylcyclohexyl) peroxydicarbonate
   25-80 wt % of ethylene glycol dibenzoate.

2. Powder formulation according to claim 1 comprising:
   50-75 wt % of di(4-tert-butylcyclohexyl) peroxydicarbonate
   25-50 wt % of ethylene glycol dibenzoate.

3. Powder formulation according to claim 2 comprising:
   60-70 wt % of di(4-tert-butylcyclohexyl) peroxydicarbonate
   30-40 wt % of ethylene glycol dibenzoate.

4. Powder formulation according to claim 1 additionally comprising 0.1-5.0 wt % of an anti-caking agent.

5. Process for the production of a powder formulation of claim 1 comprising the step of physically mixing di(4-tert-butylcyclohexyl) peroxydicarbonate powder with the ethylene glycol dibenzoate.

6. Process for curing an unsaturated polyester resin, a vinyl ester resin, or an acrylate resin comprising the step of adding the powder formulation of claim 1 to said resin and heating the resulting mixture at a temperature of 60-140 degree C.

7. Powder formulation according to claim 1 additionally comprising 0.1-5.0 wt % of silica.

* * * * *